(12) United States Patent
Hibbs et al.

(10) Patent No.: US 7,141,987 B2
(45) Date of Patent: Nov. 28, 2006

(54) SENSOR SYSTEM FOR MEASUREMENT OF ONE OR MORE VECTOR COMPONENTS OF AN ELECTRIC FIELD

(75) Inventors: Andrew D. Hibbs, La Jolla, CA (US); Robert Matthews, San Diego, CA (US)

(73) Assignee: Quantum Applied Science and Research, Inc., San Diego, CA (US)

( * ) Notice: Subject to any disclaimer, the term of this patent is extended or adjusted under 35 U.S.C. 154(b) by 0 days.

(21) Appl. No.: 10/959,479

(22) Filed: Oct. 7, 2004

(65) Prior Publication Data

US 2005/0073322 A1   Apr. 7, 2005

Related U.S. Application Data

(60) Provisional application No. 60/509,423, filed on Oct. 7, 2003.

(51) Int. Cl.
*G01R 27/26* (2006.01)
*G01R 29/12* (2006.01)

(52) U.S. Cl. .................. 324/658; 324/457; 324/686; 324/690

(58) Field of Classification Search .............. 324/658
See application file for complete search history.

(56) References Cited

U.S. PATENT DOCUMENTS

| | | | |
|---|---|---|---|
| 3,500,823 A | 3/1970 | Richardson et al. | |
| 3,565,060 A | 2/1971 | Sipple | |
| 3,620,208 A | 11/1971 | Higley et al. | |
| 3,715,660 A | 2/1973 | Ruhnke | |
| 3,722,677 A | 3/1973 | Lehnert | |
| 3,744,482 A | 7/1973 | Kaufman et al. | |
| 3,815,000 A | 6/1974 | Phillips et al. | |
| 3,880,146 A | 4/1975 | Everett et al. | |
| 3,882,846 A | 5/1975 | Fletcher et al. | |
| 3,923,042 A | 12/1975 | Hajdu et al. | |
| 3,986,109 A | 10/1976 | Poduje | |
| 4,023,408 A | 5/1977 | Ryan et al. | |
| 4,248,244 A | 2/1981 | Charnitski et al. | |
| 4,277,751 A | 7/1981 | Lawson et al. | |
| 4,346,384 A * | 8/1982 | Raab .................. | 342/451 |
| 4,419,622 A | 12/1983 | Cuneo, Jr. et al. | |
| 4,478,223 A | 10/1984 | Allor | |
| 4,569,357 A * | 2/1986 | Sanz et al. ............. | 600/512 |

(Continued)

FOREIGN PATENT DOCUMENTS

CA   2428250   11/2003

(Continued)

OTHER PUBLICATIONS

Author Unknown, "Ultra Low Input Bias Current Instrumentation Amplifier," Burr-Brown Corp., pp. 1-9, 1994.

(Continued)

*Primary Examiner*—Andrew H. Hirshfeld
*Assistant Examiner*—Timothy J. Dole
(74) *Attorney, Agent, or Firm*—Diederiks & Whitelaw, PLC

(57) ABSTRACT

A sensor system accurately measures, with a high level of sensitivity, one or more vector components of a small electric field, through the use of multiple, relatively fixed sensors, at least one of which constitutes a weakly coupled capacitive sensor. The sensor system enables the electric field to be determined in a direction normal to a surface or along multiple orthogonal axes. Measurement of the electric field vector can provide improved resolution and characterization of electrical signals produced, for example, by organs within the human body.

24 Claims, 5 Drawing Sheets

U.S. PATENT DOCUMENTS

| | | | |
|---|---|---|---|
| 4,580,576 A | 4/1986 | Blackwood | |
| 4,581,821 A | 4/1986 | Cahalan et al. | |
| 4,588,993 A | 5/1986 | Babij et al. | |
| 4,593,702 A | 6/1986 | Kepski et al. | |
| 4,602,639 A | 7/1986 | Hoogendoorn et al. | |
| 4,669,479 A | 6/1987 | Dunseath, Jr. | |
| 4,688,141 A | 8/1987 | Bernard et al. | |
| 4,733,242 A | 3/1988 | de Rose | |
| 4,785,237 A | 11/1988 | Cox | |
| 4,801,866 A | 1/1989 | Wixley | |
| 4,806,851 A | 2/1989 | Krider et al. | |
| 4,850,370 A | 7/1989 | Dower | |
| 4,873,483 A | 10/1989 | Ostrander | |
| 5,001,594 A | 3/1991 | Bobbio | |
| 5,015,906 A | 5/1991 | Cho et al. | |
| 5,036,334 A | 7/1991 | Henderson et al. | |
| 5,039,312 A | 8/1991 | Hollis, Jr. et al. | |
| 5,090,643 A | 2/1992 | Spears | |
| 5,119,404 A | 6/1992 | Aihara | |
| 5,184,215 A | 2/1993 | Barker | |
| 5,191,891 A | 3/1993 | Righter | |
| 5,229,593 A | 7/1993 | Cato | |
| 5,289,822 A | 3/1994 | Highe et al. | |
| 5,304,941 A | 4/1994 | Tateishi | |
| 5,315,232 A | 5/1994 | Stewart | |
| 5,325,073 A | 6/1994 | Hasegawa | |
| 5,336,999 A | 8/1994 | Mansfield et al. | |
| 5,458,116 A | 10/1995 | Egler | |
| 5,485,092 A | 1/1996 | Fortin | |
| 5,488,677 A | 1/1996 | Tokano | |
| 5,574,805 A | 11/1996 | Toba et al. | |
| 5,632,280 A | 5/1997 | Leyde et al. | |
| 5,645,527 A | 7/1997 | Beck | |
| 5,646,525 A * | 7/1997 | Gilboa | 324/207.17 |
| 5,650,750 A | 7/1997 | Leyde et al. | |
| 5,670,870 A | 9/1997 | Muramatsu | |
| 5,699,015 A | 12/1997 | Dotson et al. | |
| 5,734,296 A | 3/1998 | Dotson et al. | |
| 5,751,192 A | 5/1998 | Main | |
| 5,781,003 A | 7/1998 | Kondo | |
| 5,795,293 A | 8/1998 | Carim et al. | |
| 5,798,673 A | 8/1998 | Griffith et al. | |
| 5,896,035 A | 4/1999 | Takahashi | |
| 5,947,920 A | 9/1999 | Beck | |
| 6,052,615 A | 4/2000 | Feild et al. | |
| 6,096,220 A | 8/2000 | Ohkawa | |
| 6,111,466 A | 8/2000 | Mokhtar et al. | |
| 6,134,424 A | 10/2000 | Nishihori et al. | |
| 6,215,294 B1 | 4/2001 | Coleman | |
| 6,242,911 B1 | 6/2001 | Maschek | |
| 6,246,367 B1 | 6/2001 | Markson et al. | |
| 6,262,631 B1 | 7/2001 | Li | |
| 6,411,108 B1 | 6/2002 | Douglas et al. | |
| 6,438,413 B1 | 8/2002 | Taheri | |
| 6,472,888 B1 | 10/2002 | Oguma et al. | |
| 6,551,252 B1 | 4/2003 | Sackner et al. | |
| 6,597,942 B1 | 7/2003 | Yonce | |
| 6,611,168 B1 | 8/2003 | Denison et al. | |
| 6,674,281 B1 | 1/2004 | Shieh | |
| 6,686,800 B1 | 2/2004 | Krupka | |
| 6,721,591 B1 | 4/2004 | Wei et al. | |
| 6,754,523 B1 | 6/2004 | Toole | |
| 6,755,795 B1 | 6/2004 | Marmaropoulos et al. | |
| 6,760,615 B1 | 7/2004 | Ferek-Petric | |
| 6,791,311 B1 | 9/2004 | Murphy et al. | |
| 6,807,438 B1 | 10/2004 | Brun Del Re et al. | |
| 6,842,006 B1 | 1/2005 | Conti et al. | |
| 6,861,838 B1 | 3/2005 | Kawase | |
| 2002/0038092 A1 | 3/2002 | Stanaland et al. | |
| 2003/0036691 A1 | 2/2003 | Stanaland et al. | |
| 2003/0214408 A1 | 11/2003 | Grajales et al. | |
| 2003/0224685 A1 | 12/2003 | Sharma | |
| 2003/0231141 A1 | 12/2003 | Alden et al. | |
| 2004/0070446 A1 | 4/2004 | Krupka | |
| 2004/0073104 A1 | 4/2004 | Brun Del Re et al. | |
| 2004/0254435 A1 | 12/2004 | Mathews et al. | |

FOREIGN PATENT DOCUMENTS

| | | |
|---|---|---|
| GB | 2353594 | 2/2001 |
| WO | 03/048789 | 6/2003 |
| WO | 03/079897 | 10/2003 |

OTHER PUBLICATIONS

Byrne et al., "Ground-Based Instrumentation for Measurement of Atmospheric Conduction Current and Electric Field at the South Pole," Journal of Geophysical Research, vol. 98, No. D2, pp. 2611-2618, Feb. 20, 1993.

Clippingdale et al., "Ultra-High Impedance Voltage Probes and Non-Contact Electrocardiography," Sensors: Technology, Systems and Applications, 1st Edition, IOP Publ. Ltd., pp. 469-472, 1991.

Clippingdale et al., "Non-Invasive Dielectric Measurements with the Scanning Potential Microscope," J. Phys. D: Appl. Phys., IOP Publ. Ltd., vol. 27, pp. 2426-2430, 1994.

Clippingdale et al., "Ultrahigh Impedance Capacitively Coupled Heart Imaging Array," Rev. Sci. Instrum., American Institute of Physics, vol. 65, No. 1, pp. 269-270, Jan. 1994.

Geddes, L. A., "Electrodes and the Measurement of Bioelectric Events," Wiley-Interscience, pp. 97-106, 1972.

Harland et al., "Electric Potential Probes—New Directions in the Remote Sensing of the Human Body," Meas. Sci. and Technol., Institute of Physics Publishing, IOP Publ. Ltd., vol. 13, pp. 163-169, 2002.

Harland et al., "Remote Detection of Human Electroencephalograms Using Ultrahigh Input Impedance Electric Potential Sensors," Applied Physics Letters, American Institute of Physics, vol. 81, No. 17, pp. 3284-3286, Oct. 2002.

Harland et al., "High Resolution Ambulatory Electrocardiographic Monitoring Using Wrist-Mounted Electric Potential Sensors," Meas. Sci. and Technol., Institute of Physics Publishing, IOP Publ. Ltd., vol. 14, pp. 923-928, 2003.

Harrison, "An Antenna Electrometer System for Atmospheric Electrical Measurements," Rev. Sci. Instrum., American Institute of Physics, vol. 68, No. 3, pp. 1599-1603, Mar. 1997.

Horowitz et al. "The Art of Electronics," 2nd Edition, Cambridge University Press, pp. 96-98, 183-187, 193-207, 209-210, 1989.

Maynard, "Electric Field Measurements in Moderate to High Density Space Plasmas with Passive Double Probes," Geophysical Monograph, American Geophysical Union, vol. 103, pp. 13-27, 1998.

Nunez, P. L., "Electric Fields of the Brain: The Neurophysics of EEG," Oxford Univeristy Press, pp. 197-198, 1981.

Nunez, P.L. et al. "Spatial-Temporal Structures of Human Alpha Rhythms: Theory, Microcurrent Sources, Multiscale Measurements, and Global Binding of Local Networks," Human Brain Mapping, Wiley-Liss, Inc., vol. 13, pp. 125-164, 2001.

Pederson, "Electric Field Measurements in a Tenuous Plasma with Spherical Double Probes," Geophysical Monograph, American Geophysical Union, vol. 103, pp. 1-12, 1998.

Prance et al., "Electrometer Arrays: Sensing of Spatio-Temporal ELF Fields," Proc. Marelec, 3.4, 1997.

Prance et al., "Non-Contact VLSI Imaging Using a Scanning Electric Potential Microscope," Meas. Sci. Technol. vol. 11, pp. 1229-1235, 1998.

Prance et al., "An Ultra-Low-Noise Electrical-Potential Probe for Human-Body Scanning," Meas. Sci. and Techol., IOP Publ. Ltd., vol. 11, pp. 1-7, 2000.

Richardson, P.C., "The Insulated Electrode: A Pasteless Electrocardiographic Technique," 20th Annual Conference on Engineering in Medicine and Biology, pp. 15.7, 1967.

Srebo, R., "Localization of Visually Evoked Cortical Activity in Humans," J. Physiology, vol. 360, pp. 233-246, 1985.

Srinivisan et al., "Spatial Sampling and Filtering of EEG with Spline Laplacians to Estimate Cortical Potentials," Brain Topography, Human Sciences Press, Inc., vol. 8, No. 4, pp. 355-366, 1996.

Von Helmholtz, H., Ann. Phys. Chem., vol. 29, pp. 211-233, 1853.

Clayton et al., "Absolute Calibration of Antennas at Extremely Low Frequencies," IEEE Transactions on Antennas and Propagation, vol. AP-21, No. 4, pp. 514-523, Jul. 1973.

Degauque et al. (Editors), "Electromagnetic Compatibility," Simulation Techniques and Sensors, Oxford University Press, pp. 614-643, 1993.

Filloux, "Electric Field Recording on the Sea Floor with Short Span Instruments," J. Geomag. Geoelectr., vol. 26, pp. 269-279, 1974.

Hill et al., "Electric Field Strength," The Measurement, Instrumentation, and Sensors Handbook, IEEE Press, pp. 47.1-47.13.

* cited by examiner

SENSOR SYSTEM FOR MEASUREMENT OF ONE OR MORE VECTOR COMPONENTS OF AN ELECTRIC FIELD

CROSS-REFERENCE TO RELATED APPLICATION

The present application claims the benefit of U.S. Provisional Patent Application Ser. No. 60/509,423 entitled "Integrated Electric and Magnetic Field Sensor" filed Oct. 7, 2003.

BACKGROUND OF THE INVENTION

1. Field of the Invention

The present invention pertains to measuring small electric fields and, more particularly, to a sensor system for measuring one or more vector components of an electric field generated by an object in a non-conducting or poorly conducting medium utilizing at least one capacitive electric sensor which is spaced from the surface of the object and mounted a predetermined distance from another sensor.

2. Discussion of the Prior Art

It is widely known that electric fields are developed from many different sources. For example, organs in the human body, including the heart and brain, produce small electric fields. In addition, there is a need to measure larger electric fields produced in other areas, such as geophysics and power lines at ranges where the fields are small. For a variety of reasons, it can be desirable to measure these electric fields. The prior art has focused on methods of measuring the distribution of electric potentials on conducting surfaces by burying or otherwise inserting metal rods into the ground in the case of geophysical measurements at the earth's surface, and using gel-coated electrodes placed directly on the skin of a patient in the case of measurements taken in the practice of medicine. In either case, the measurement instruments, e.g., the metal rods or electrodes, are in direct contact with the surface. Taking measurements of the electric potential at a position spaced from a surface is more demanding. Additional difficulties arise in measuring a field normal to a conducting surface or measuring multiple orthogonal components of an electric field, particularly when one of those components is not parallel to a local conducting surface. Although some prior art exists in connection with determining maximum electric fields by measuring multiple components of the fields, such as represented in U.S. Pat. No. 6,242,911, these arrangements address large electric fields, such as those associated with power generation equipment. Indeed, such arrangements are specifically designed to have reduced sensitivity and are not suited to measure small fields.

It should be realized that the terms electric field and electric potential at a point in space are sometimes used as if they are synonymous. This represents a technical error of convenience in the sense that what is often actually measured is the electric potential relative to some other voltage. The terms are equivalent in the sense that this measured potential would not differ from the voltage to which it is compared if an electric field were not present. As a result, the terms electric potential and electric field are sometimes used interchangeably in the literature, often inaccurately. Indeed, although it might be stated that an electric field is measured, it may actually be the time variation of the potential that is measured. In the majority of cases, electric potentials are simply measured relative to a common potential of no well-defined physical position (often termed the "ground") and a simple map of these potentials recorded by plotting the potential values at the specific measurement positions relative to the common reference is produced.

Some work has been conducted in connection with measuring cardiac waveforms, with some equivalent work also being done on imaging the potentials produced by electrical circuit boards. An area of considerable scientific and commercial importance that could be significantly improved by the measurement of multiple components of the electric field is the characterization of electrical activity in the human body. In the current practice, a set of electric potential measurements are taken at desired points on the skin via electrically conducting contacts, or capacitive coupling with a high value of capacitance created when the sensors are directly attached to the skin. The former contacts are made by conducting electrodes that touch the skin, with considerable effort being made to ensure a reliable resistive contact. The latter are made by insulated electrodes that also touch the skin in order to ensure a high value of the mutual capacitance. The resulting time-varying distribution of skin surface potentials has been effectively used in diagnosing heart disease and mapping brain functions.

However, interpretation of the surface potential can be complicated since a given surface potential distribution may be generated by more than one source. In other words, the implications about the underlying source may not be unique. One way to augment present measurements on the body surface would be to measure the electric field ($E_n$) in a direction normal to the body. Because contact to the skin is required, conventional electrodes touching the skin cannot measure the electric potential off the body, and therefore cannot measure the electric field $E_n$.

To address the problem of a lack of uniqueness, physical assumptions and mathematical operations have been used to estimate the underlying electrical sources from the measured surface electric potential distribution. A particular practical example is high-resolution electroencephalogram (EEG) which estimates the distribution of electrical activity at the brain surface from measurements taken directly at the outer surface of the scalp. If a dense array of surface electrodes is used, e.g., a 64- or a 131-channel EEG, a surface Laplacian function can be estimated to improve EEG spatial resolution. For example, the surface Laplacian method applied to 131-channel EEG signals has achieved spatial resolution in the 2-cm range.

It should be noted that capacitive electric potential sensors have also been used to collect simultaneous recordings of electric potential at points spaced from a surface. However, all of these prior measurements have been performed at an equal distance to a conducting surface, e.g., a human body, and did not measure the component of the E-field normal to that surface. Capacitive sensors have also been used on either side of the human body (one about 35 cm from the chest and one about 35 cm from the back) to detect a human heartbeat with electric potential sensors from a considerable distance. However, still no attempt has been made to derive the electric field from the potential measurements or to measure a vector component of the electric field normal to the body surface.

When considering the overall task of measuring the normal vector of the electric field of an object at a position spaced from the object, certainly the compact nature of the sensor system will be of concern, with more compact arrangements being highly favorable, particularly in the medical field. In any case, it should be realized that the electric fields of concern are small, generally much less than 1 volt/meter, such that any reliable information from sensed measurements spaced from the object would require a high level of sensitivity. Based on the above, there exists a need for a compact sensor system that can be employed to effectively and conveniently measure one or more vector components of a small electric field associated with an object, such as for medical purposes, with a high level of sensitivity, utilizing at least one capacitive electric sensor which is spaced from the object.

SUMMARY OF THE INVENTION

The present invention is directed to a sensor system for determining one or more components of a small electric field associated with an object by using a capacitive sensor in combination with either a resistive-type sensor or another capacitive sensor to determine magnitude and direction (vector) information of the electric field. The sensor system can be employed to determine a single E-field component normal to a surface of the object or multiple orthogonal components of the electric field. In either case, the two sensors are maintained at a fixed distance apart for generating first and second electric potential signals from which the vector information is determined.

In accordance with a preferred embodiment of the invention, electric potentials are measured by the capacitive and other sensors at two defined points which are no more than 5 cm apart, while preferably having a sensitivity relative to their input in the range of about $1 \text{ mV/Hz}^{1/2}$ at 1 Hz, in order to determine the electric field. The capacitive sensor preferably includes a flat conducting surface that couples capacitively to the local electric potential, serving to sense the potential, with the flat conducting surface being electrically insulated to prevent the flow of a real electrical current.

In accordance with the most preferred embodiment of the invention, multiple sensors are employed for measuring the electric potential, with the multiple sensors being preferably, rigidly connected together. In one embodiment, the sensors are arranged to determine a vector component of the electric field normal to the object. In another embodiment, the sensors are arranged along at least two orthogonal axes to determine multiple vector components of the electric field. In a further embodiment, the sensors are specifically arranged along predetermined axes from which orthogonal components of the electric field can be readily determined. In any case, the time varying nature of a small electric field can be measured with a high level of sensitivity, while processing both magnitude and directional data significantly enhances the information needed for diagnostic and other evaluation purposes.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1:
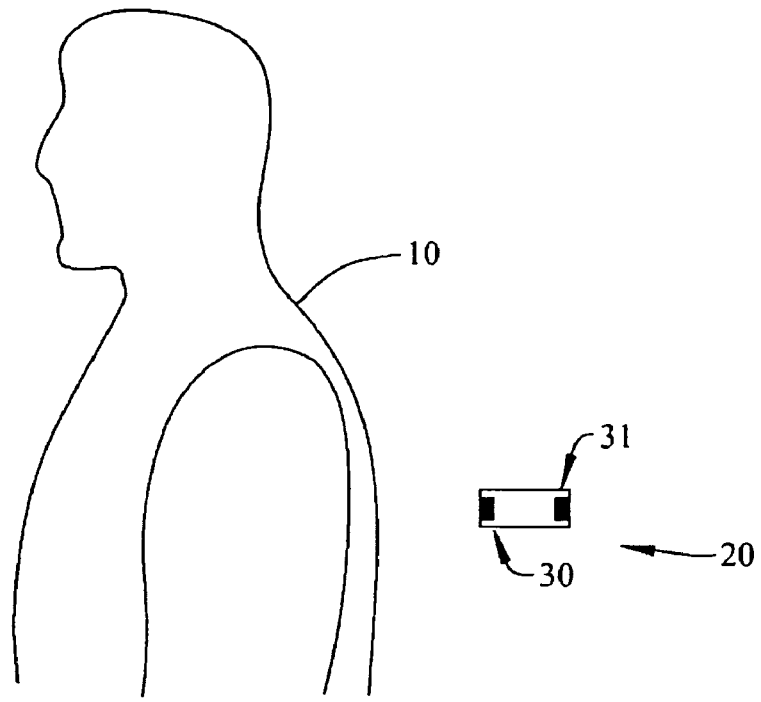
FIG. 1 is a schematic diagram showing the measurement of an electric field normal to a human body using a capacitive sensor constructed in accordance with the invention, with each of the sensors being spaced from the body.

Initially, it is important to note that an object placed in an electric field rises to the potential associated with the field, at least at its geometric center. FIG. 1 illustrates the invention used in connection with measuring an electric field produced outside of a human body 10, such as the heart (not shown) of human body 10. To sense the electric field in accordance with the invention, a sensor system, generally indicated at 20, is positioned adjacent to body 10. As shown, sensor system 20 includes a plurality of sensors, two of which are indicated at 30 and 31. Sensors 30 and 31 are fixed a predetermined distance apart and employed to measure electric potentials associated with body 10. The invention is, at least partially, predicated on the fact that the capacitance of an object is dominated by its mutual capacitance to objects in close proximity, with the capacitance reverting to a free-space capacitance, as the object is isolated. For an object of maximum size of about 1 cm, the free-space capacitance is in the order of 1 pF. If the object is placed very close to another conducting object and further separated by an insulator with a high dielectric constant, the capacitance of the object per unit area of its surface in close proximity can be of order $1 \text{ nF/cm}^2$.

In accordance with the invention, an object is considered to be weakly coupled to the local electric potential if its capacitance is less than 10 pF. It has recently become possible to make measurements in the weakly coupled capacitive regime at a sensitivity level of order 10 μV. This has been made possible through advances in solid-state electronic devices and circuit designs such as set forth in U.S. Pat. No. 6,680,800 and U.S. Patent Application Publication 2004/007446, both of which are incorporated herein by reference. The present invention provides further advances in connection with establishing a compact sensor system 20 that can measure one or more vector components of the electric field at very high sensitivity. To measure the electric field, it is only necessary to measure the potential at two points, subtract one result from the other, and divide by the physical distance, d, between the two points, with k being readily determinable by testing the sensor in a known field.

$$E = k \frac{V_1 - V_2}{d}. \quad [1]$$

As will be detailed more fully below, the two measurements can be made by completely different sensors or by connecting two separate potential sensors to an appropriate amplifier with a differential input. The voltage of one sensor can be subtracted in a pair-wise fashion from multiple other sensors to provide the electric field in the direction of the vector joining the measurement points according to the above equation. The electric potential at a point or over a surface can be recorded as a time-varying potential map, without constructing electric field vectors relative to the common ground, or between the points.

By a "compact" sensing system it is meant that the region over which the field is measured is small relative to the spatial variations in the field that are of interest, and/or is sufficiently compact that a system that measures multiple components of the field is of a convenient size, i.e., having a maximum size less than 75 cm. An example of the former criterion is the measurement of the electric fields produced by the human body, which are expected to vary over distances in the order of 3 cm and must accordingly be measured by sensors of equal or smaller size. In addition, such electric fields are small, typically ranging from less than 1 volt/meter to 1 micro-volts/meter at approximately 1 Hz. In fact, the sensor system of the invention is designed with a high sensitivity for use in measuring small electric fields even in the order to 0.1, 0.01, 0.001 and 0.0001 volts per meter at approximately 1 Hz. A particular application of the invention in the field of medicine is to utilize a capacitive potential measurement of the electric field at some separation from the body in conjunction with a second simultaneous electric potential measurement along the same normal vector to the body but at a different separation (or other simultaneous measurement(s) such that the signal contribution along the same normal vector is sufficient and known) in order to measure $E_n$.

Figure 2:
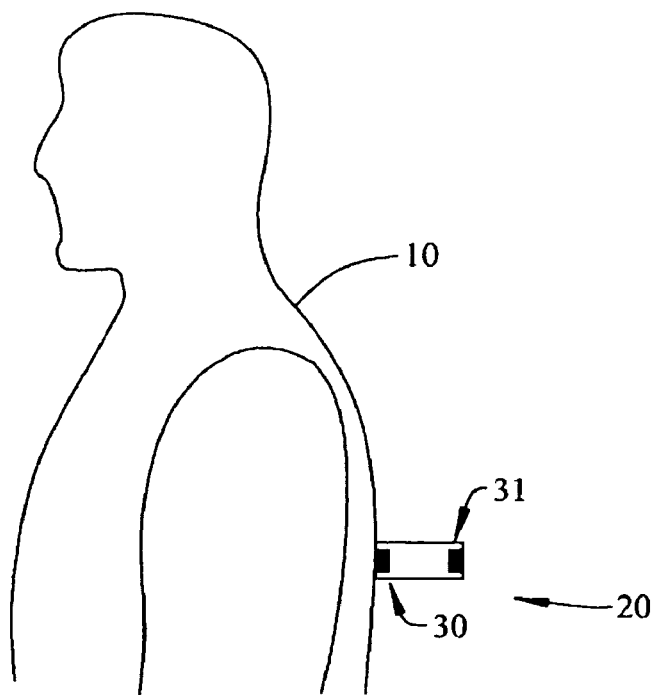
FIG. 2 is a schematic diagram similar to FIG. 1, illustrating the measurement of the electric field normal to the body, with one sensor being in contact with the body.

In FIG. 1, a measurement of $E_n$ is made using sensor system 20 having weakly coupled sensors 30 and 31. As shown, both of sensors 30 and 31 are spaced from body 10 so as not to be in contact with body 10. Although this arrangement is preferred, FIG. 2 illustrates a potential configuration wherein sensor 30 is placed in contact with body 10. With this arrangement, sensor 30 need not constitute a capacitive sensor per se, but rather could be either a capacitive or resistive type sensor. In any case, at least sensor 31 constitutes a capacitive sensor. Regardless, the information on the electric field associated with body 10 in a direction normal to its surface can be used to augment information obtained from measured tangential electric fields. Additional sensors, preferably capacitive sensors, can also be provided in sensor system 20 to measure electric field information along additional axes as further discussed below.

As indicated above, the invention concerns a sensor system for measuring one or more components of an electric field, with at least one vector component being measured by a weakly coupled capacitive sensor. The sensor system is compact and used to perform a weakly coupled capacitive measurement of the electric potential at a sensitivity level needed to record small electrical signals, such as from a human heart or brain. The sensor system must enable measurement of the electric field in free-space, without conducting or high capacitive coupling to any conducting surface. The compact nature of the sensor system means that the part of it that couples to the free-space electric potential has a capacitance in the range of about 0.1 pF to 2 pF.

Figure 3:
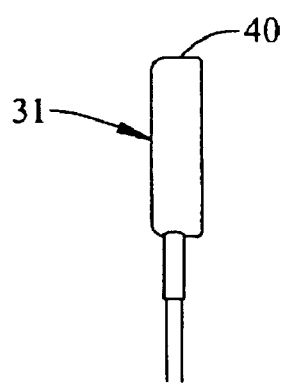
FIG. 3 is a side view of one of the capacitive sensor elements of FIGS. 1 and 2.
Figure 4:
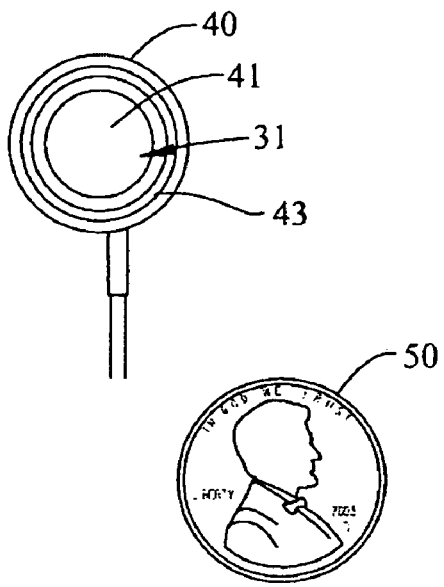
FIG. 4 is a front elevational view of the capacitive sensor element of FIG. 3 shown in size relation to a coin.

Reference will now be made to FIGS. 3 and 4 in referencing the compact nature of sensor 31. In this example, first stage electronics, which will be discussed further below, are enclosed within a housing 40 of sensor 31. As shown, sensor 31 includes an electrode 41 that takes the form of a substantially flat disk. Electrode 41 is isolated from housing 40 by an insulator 43. In addition, electrode 41 is insulated from internal components (not shown) by materials having high electrical resistance and, in some system embodiments, guard surfaces. To give the reader an idea of the size of sensor 31, a coin (U.S. penny) 50 is shown in relation to sensor 31 in FIG. 4.

Figure 5:
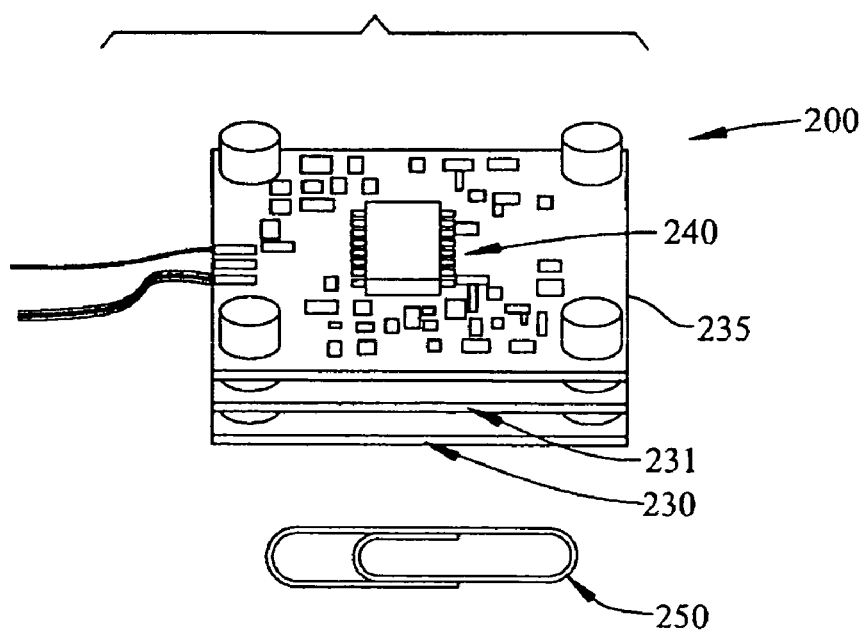
FIG. 5 is a perspective view of internal components of a capacitive sensor built in accordance with a preferred embodiment of the invention.

FIG. 5 illustrates another compact single-axis E-field capacitive sensor system 200 particularly designed for measuring the electric field normal to human body 10. As shown, two sensors 230 and 231 are established by circuit boards positioned in parallel planes about 1 cm apart. A third layer 235 of sensor system 200 carries the electronic components, such as indicated at 240 for high-impedance buffering and analog differencing. Sensor system 200 can be combined with conventional skin-contacting resistive or capacitive sensors, in a manner corresponding to that set forth above, or similarly constructed, weakly coupled capacitive sensors to provide a measure of multiple orthogonal components of the E-field. To this end, sensors 230 and 231 are analogous to sensors 30 and 31 discussed above and are used in combination to sense a vector component of a small electric field, preferably in connection with body 10, with a high level of sensitivity.

For measuring the component(s) of the electric field, sensors 230 and 231 of capacitive sensor system 200 are orientated relative to each other in a predetermined manner. Most preferably, sensors 230 and 231 are rigidly connected together at a fixed distance. In addition, in a manner which also applies to sensor system 20, sensor system 200 is compact in that its spatial extent in any direction does not exceed approximately 5 cm and, more preferably, less than 3.5 cm. Again, to give the reader an idea of the size of sensor system 200, a paper clip 250 is shown in relation to sensor system 200. By way of example, certain individual sensors which could be employed in the invention are disclosed in U.S. patent application Ser. No. 10/459,267 entitled "Sensor Systems For Measuring Biopotentials" filed Jun. 11, 2003 which is hereby incorporated by reference.

Figure 6:
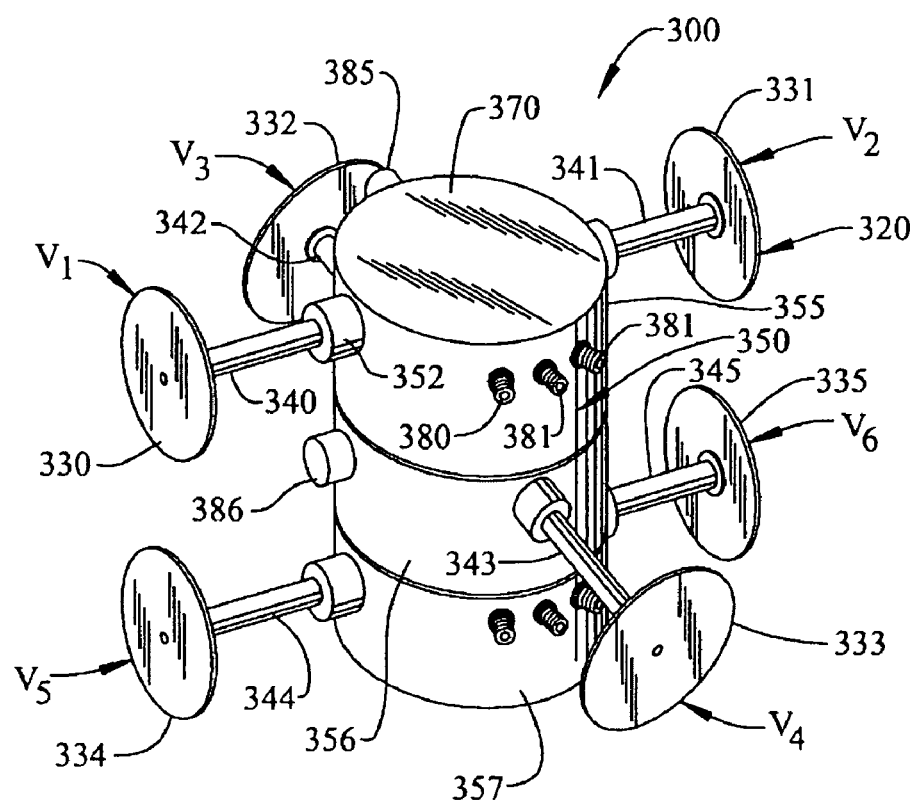
FIG. 6 is a perspective view of a capacitive sensor constructed in accordance with another embodiment of the invention that measures multiple orthogonal components of an electric field.

An example of a multi-axis E-field sensor system 300 built according to another embodiment of the invention is shown in FIG. 6. In this system, three orthogonal axes of an electric field are measured with various capacitive sensors 330–335 arranged as pairs in orthogonal oriented directions. As shown, each of the six sensors 330–335, which preferably take the form of conducting plates, functions to measure an electric potential in the form of a respective voltage $V_1$–$V_6$ at its geometric center. More specifically, sensors 330–335 are linked and maintained at fixed relative positions through respective support arms 340–345 to a main body or housing 350 through insulators, such as that indicated at 352 for support arm 340. In the most preferred form of the invention, housing 350 is formed from attaching three individual sensor modules 355–357, with sensors 330 and 331 being carried by module 355; sensors 332 and 333 being carried by module 356; and sensors 334 and 335 being carried by module 357. Support arms 340 and 341 are preferably coaxially aligned along a first axis, while support arms 342 and 343 extend coaxially along a second axis and support arms 344 and 345 extend coaxially along a third axis. As shown, the second axis associated with support arms 342 and 343 is arranged substantially perpendicular to the first and third axes.

Housing 350 also includes first and second end caps, one of which is indicated at 370. Within housing 350 is the electronics (not shown) associated with sensor system 300 that provide for a first stage high-impedance amplification as will be detailed below. Also projecting from each module 355–357 are respective electrical connectors, such as those indicated at 380–382 for module 355. Electrical connectors 380–382 are provided to link each module 355–357 of housing 350 to electrical components employed in reading and evaluating the signals received from sensor system 300. In addition, each module 355–357 includes an associated power switch, such as power switches 385 and 386 for modules 355 and 356 respectively. At this point, it should be understood that housing 350 could be integrally constructed, while employing only one set of electrical connectors 380–382 and one power switch 385, 386.

With this arrangement, electric fields are constructed in the following manner: $E_X=k_x(V_1-V_2+V_5-V_6)/2$, $E_Y=k_Y(V_3-V_4)$, $E_Z=k_Z(V_1+V_2-V_5-V_6)/2$ in which the plate voltages $V_i$ and the constants $k_i$ are determined by calibration in a known electric field prior to actual use of sensor system 300. By virtue of the design of the capacitive-type, multi-component electric field sensor system 300 represented in FIG. 6, the three measured field components Ex, Ey and Ez intersect centrally in modules 355–357 of housing 350. However, it should be noted that the individual sensing arrays established by sensors 330–335 need not be arranged perpendicular with respect to each other, but rather only sufficient projection in orthogonal directions is needed to estimate the fields in those orthogonal directions. Multiple sensors of the invention may also be grouped together to measure, for example, vector components of small electric fields produced by the brain at multiple points around the head of an individual. In addition, multiple separate units may be used to determine all three components of the electric field from a collection of two-axis measurements.

Figure 7:
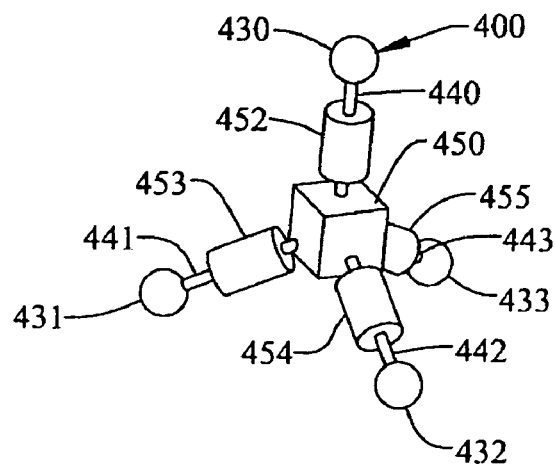
FIG. 7 is a perspective view of a capacitive sensor constructed in accordance with a further embodiment of the invention that measures non-orthogonal components of an electric field.

FIG. 7 shows a capacitive-type, multi-component electric field sensor system 400 constructed in accordance with a further embodiment of the invention. Sensor system 400 is basically presented to illustrate that the field measurements need not be made along purely orthogonal axes. Instead, if desired, the field components in orthogonal directions can be calculated via simple geometry by methods well known in the art. To this end, note that sensor system 400 includes sensors 430–433, a housing 450, support arms 440–443 and insulators 452–455. With this arrangement, various components of an electric field can be sensed by sensors 430–432 and the signals therefrom can be processed to establish orthogonal electric field measurements through simply knowing the geometrical relationship between sensors 430–433. Therefore, sensor system 400 can operate in a manner corresponding to sensor system 300, with fewer support arms and sensors, while requiring some mathematical manipulation of the signals from sensors 430–433 to arrive at corresponding electric field data.

Figure 8:
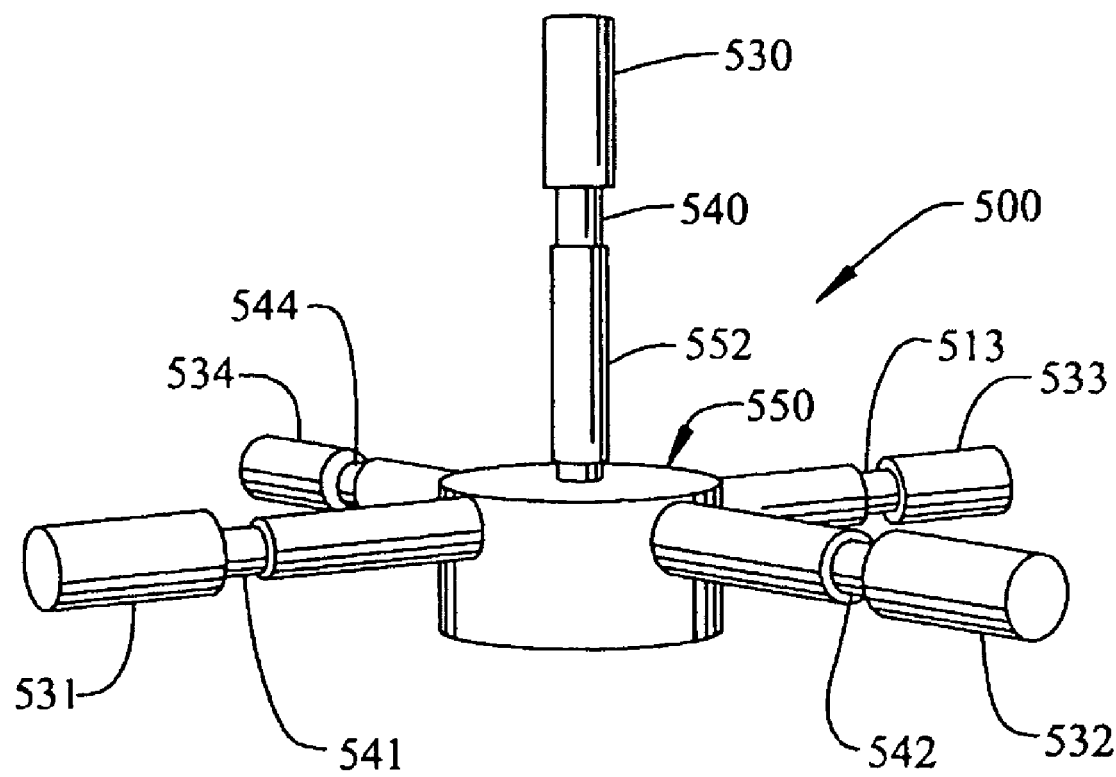
FIG. 8 is a perspective view of a capacitive sensor constructed in accordance with a still further embodiment of the invention that measures orthogonal components of an electric field.

FIG. 8 presents a still further embodiment of the invention wherein a sensor system 500 includes a plurality of sensors 530–534 which are supported from a generally puck-shaped housing 550 through respective support arms 540–544. Each support arm 540–544 has associated therewith a respective insulator, one of which is indicated at 552 for support arm 540. The electric potential sensor is now self-contained in the sense that the first stage high input impedance electronics that was formerly located in housing 350 is now located with housing 530. The difference in the outputs of these sensors can be combined as in Equation 1 set forth above, to produce the value of the E-field between them.

Sensor system 500 shows a total of five electric potential sensors 530–534. In this embodiment, the field along the vertical axis of the sensor is calculated by subtracting the output of sensor 530 from the average of the outputs of sensors 531–534. If desired, a sixth sensor (not shown) can be positioned on housing 550 of magnetic sensor 552 or on an extension that protrudes below housing 550 to provide a single measurement point for the second potential measurement along the vertical axis. The advantage of the five sensor embodiment 500 shown in FIG. 3 is that, by not having a sensor in the lower part of the system, a mounting means can be positioned there instead.

As with the other embodiments disclosed, sensor system 500 is preferably battery powered. The signals recorded by each sensor 530–534 is made relative to the battery voltage that powers sensor system 500. When the common points of the batteries of any two sensors are connected together, the difference of the sensor outputs gives a reading directly proportional to the electric field. In a preferred version of the multi-axis system, one battery unit (not shown) is used for sensors 530–534, thereby ensuring that all measurements are relative to a common reference. In any case, using the approach of FIG. 8 advantageously enables electric potential sensors 530–534 to be situated at any desired position on the surface of body 10.

As should be readily apparent from the description set forth above, the invention is concerned with the integration of a free-space capacitive electric potential sensor with another capacitive or resistive sensor measurement of the electric potential to determine one or more vector components of an electric field. The invention can employ a single pair of sensors which are mounted in a fixed, well defined spatial relationship for movement in unison relevant to the object producing the electric field in order to sense a single component of the electric field normal to the object or numerous additional sensors can be employed to determine multiple orthogonal components of the electric field. The orthogonal components can be directly sensed based on the positioning of various pairs of sensors, or the sensors can be arranged along non-perpendicular axes, in which case the orthogonal components can be mathematically determined based on the established geometry. Of course, one common sensor can be utilized in combination with two or more other sensors along the desired axes. In any case, the potential signals can be used to determine vector components (magnitude and direction) of the electric field, with the overall sensing system employing at least one capacitive-type electrical sensor which is used to sense electrical potentials at a position spaced from the object. By providing an extremely compact sensor system, use of the invention in particular environments, such as the medical field, is enhanced. Utilizing capacitive-type electrical sensors enables one or more components of an electric field generated by an object, such as a human body, to be advantageously sensed in a noninvasive and unobtrusive manner.

Figure 9:
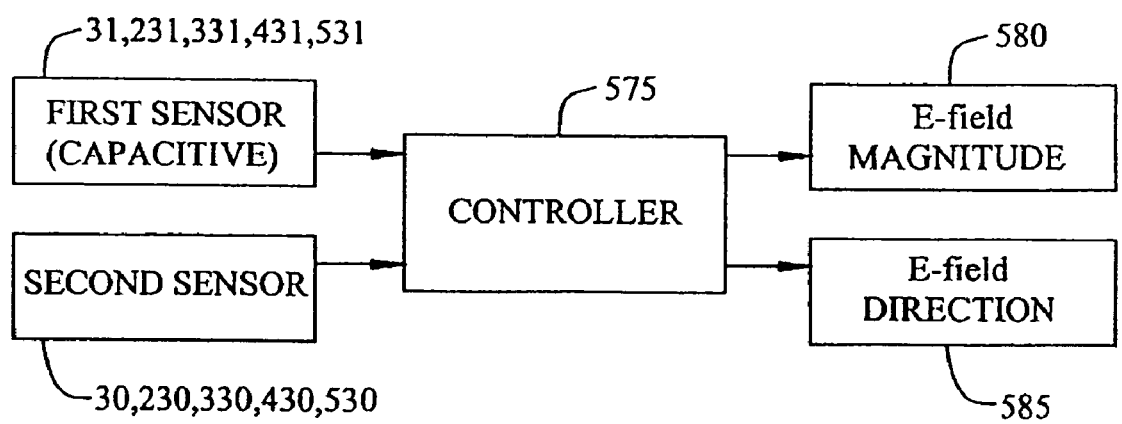
FIG. 9 is a block diagram illustrating the invention.

As the particular circuitry employed in connection with the sensor system is not part of the present invention, it will not be described in detail here, but rather reference is again be made to the U.S. patent and patent publications set forth above and incorporated herein by reference. However, FIG. 9 generally illustrates basic aspects of the present invention wherein a first capacitive-type sensor 31, 231, 331, 431, 531 sends potential signals to a controller 575, along with a second sensor 30, 230, 330, 430 and 533, in order that the signals can be processed to determine one or more vector components of the electric field as represented by E-field magnitude 580 and E-field direction 585. On a general note, a high-impedance amplifier is connected to each sensor. The amplifier is configured to buffer the potential of the sensor and send a signal representative of the potential to a subsequent low-impedance circuit. The high-impedance amplifier in the capacitive sensor preferably has an impedance, including all circuit components, of greater than 100 MΩ at the frequency of the signal of interest. In any case, the coupling of each sensor is preferably modulated in time in order to increase its sensitivity.

Figure 10:
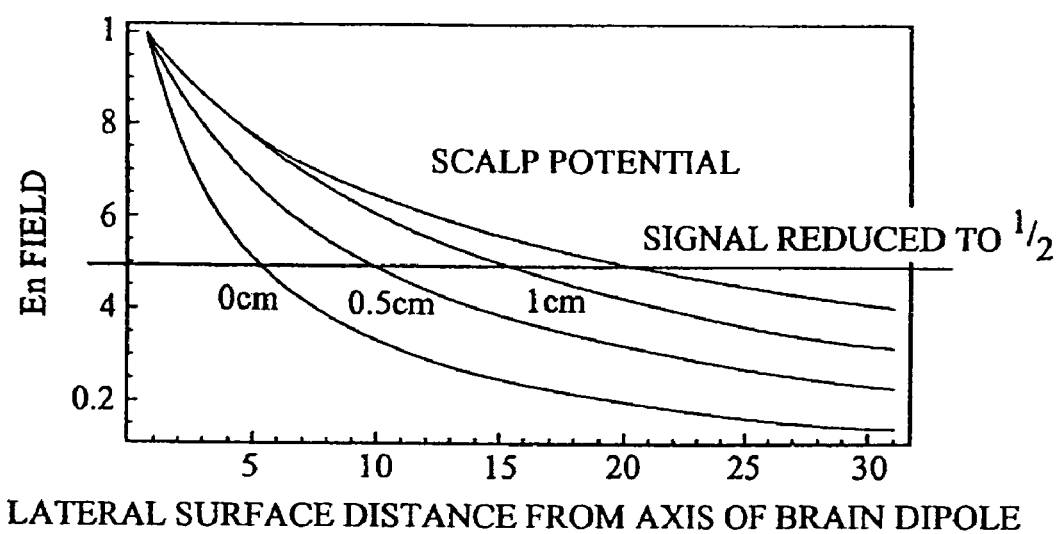
FIG. 10 is a graph showing variations of the normal E-field outside a human's head for a dipole source inside the brain as a function of lateral distance across the scalp for different normal distances from the scalp.

FIG. 10 shows a calculation of the normal E-field versus lateral surface position at different normal distances {0, 0.5, 1 cm} from a human scalp for a standard EEG dipole source, as compared to the scalp surface potential. For clarity, each measure has been normalized with respect to its individual maximum at the location directly above the dipole. This diagram shows that, for a sensor located 0.5 cm from the scalp, the point at which the signal is reduced by one-half occurs at a radial distance 2 times smaller than with a conventional surface measurement of scalp potential. As the sensor is made more compact, such that the E-field can be measured closer to the scalp, the benefit of the normal field is further increased. Thus, by enabling a measurement of the E-field on a preferred scale of 1 cm or less, the invention makes available a physical channel of information from the brain that has inherently higher spatial resolution than the prior surface contact measurement of the parallel E-field.

Although the ability to localize the source using the $E_n$ measurements at 0 cm, 0.5 cm and 1 cm represents an improvement over the scalp potential, the variation of $E_n$ with lateral distance is less focused about the axis of the source of the field than could be theoretically achieved by a surface Laplacian solution of the surface potential distribution on the scalp. However, the large number of electrodes (>40), considerable set up time and costs in terms of ancillary data acquisition equipment of prior arrangements over-shadow any potential benefits. The accuracy of the present sensor system is not negatively affected by local variations in thickness and conductivity, nor is it as sensitive to noise in the original data, verses the known prior art. In particular, the normal E-field is the direct output of a measurement so as to be less affected by these practical effects and is highly sensitive. Further, the addition of a measurement of the normal E-field to an existing surface potential measurement results in reduced artifacts related to the position of the reference electrode used with a conventional surface measurement. Reference artifacts occur in conventional EEG because: (a) the locations of brain sources are generally not known so one cannot reliably place a reference electrode that is electrically "far" from all sources, and (b) sources of EEG are typically distributed throughout large regions of neocortex and distant sources can make large contributions to local potentials if they are electrically close as a result of shunting by lower resistance paths. Taking the difference between two electrodes arranged at well defined spaced positions along an axis, orthogonal or otherwise, outside the body greatly reduces reference artifacts, leading to improved interpretation of brain electrical sources.

It should be understood that these benefits for EEG are also applicable to other medical applications, such as imaging of the heart or localization and discrimination of multiple electrical sources within the body. Furthermore, the benefits of a multi-axis E-field measurement can be expected to impact other applications, such as surveillance and geophysics. To this end, the sensor system of the present invention can also incorporate one or more magnetic sensors for simultaneously or individually sensing magnetic field data. In particular, the measurement of the field in the direction perpendicular to the ground can provide information about sources under the ground in an analogous manner to applications in the human body.

Although described with reference to preferred embodiments of the invention, it should be readily understood that various changes and/or modifications can be made to the invention without departing from the spirit thereof. One example is measuring an electric field normal to a human body and combining this data with measurements made on the surface of the skin to provide additional information about electrical activity and electrical properties of the heart, brain, and other organs. In general, the invention is only intended to be limited by the scope of the following claims.

We claim:

1. A compact sensor system for measuring at least one component of a small electric field generated by an object comprising:

a first, capacitive-type electrical sensor adapted to generate first electric potential signals related to the electric field at a first position spaced from the object;

a second electrical sensor located at a second position which is spaced a predetermined, fixed distance from said first position and does not depend on the object generating the small electric field, said second electrical sensor being adapted to generate second electric potential signals related to the electric field; and a controller for processing the first and second electric potential signals to determine a first vector component, having both a magnitude and a direction, of the electric field.

2. The sensor system according to claim 1, wherein the second electrical sensor contacts the object when producing the second electric potential signals.

3. The sensor system according to claim 1, wherein the first vector component is normal to the object.

4. The sensor system according to claim 1, wherein the small electric field is less than 1 volt per meter at 1 Hz.

5. The sensor system according to claim 1, wherein the small electric field is less than 0.1 volts per meter at 1 Hz.

6. The sensor system according to claim 1, wherein the small electric field is less than 0.01 volts per meter at 1 Hz.

7. The sensor system according to claim 1, wherein the small electric field is less than 0.001 volts per meter at 1 Hz.

8. The sensor system according to claim 1, wherein the small electric field is less than 0.0001 volts per meter at 1 Hz.

9. The sensor system according to claim 1, further comprising:

a housing supporting the first and second electrical sensors; and an insulator positioned between the first and second electrical sensors.

10. The sensor system according to claim 1, wherein the sensor system has a spatial extent in any direction which does not exceed approximately 5 cm.

11. The sensor system according to claim 1, wherein the second electrical sensor constitutes a skin-contacting, resistance-type sensor.

12. The sensor system according to claim 1, further comprising:
 a third, capacitive-type electrical sensor adapted to generate third electric potential signals related to the electric field at a position spaced from the object; and
 a fourth, capacitive-type electrical sensor adapted to generate fourth electric potential signals related to the electric field at a position spaced from the object, said controller being connected to the third and fourth electrical sensors for processing the third and fourth electric potential signals to determine a second vector component of the electric field.

13. The sensor system according to claim 12, wherein the first and second vector components are orthogonal to one another.

14. The sensor system according to claim 12, further comprising:
 a fifth, capacitive-type electrical sensor adapted to generate fifth electric potential signals related to the electric field at a position spaced from the object; and
 a sixth, capacitive-type electrical sensor adapted to generate sixth electric potential signals related to the electric field at a position spaced from the object, said controller being connected to the fifth and sixth electrical sensors for processing the fifth and sixth electric potential signals to determine a third vector component of the electric field.

15. The sensor system according to claim 12, wherein the first, second, third and fourth electrical sensors are rigidly interconnected.

16. The sensor system according to claim 15, further comprising:
 a housing; and
 a plurality of arms projecting from the housing, each of the plurality of arms supporting a respective one of the first, second, third and fourth electrical sensors.

17. The sensor system according to claim 16, wherein the housing is formed from multiple modules which are interconnected together.

18. The sensor system according to claim 17, wherein the multiple modules includes a first module from which extend the first and second electrical sensors and a second module from which extend the third and fourth electrical sensors.

19. The sensor system according to claim 18, further comprising:
 a first insulator positioned along one of the plurality of arms, between the first and second electrical sensors; and
 a second insulator positioned along another one of the plurality of arms, between the third and fourth electrical sensors.

20. The sensor system according to claim 16, wherein the plurality of arms includes first and second sets of arms, with the first and second sets of arms extending in distinct orthogonal directions.

21. The sensor system according to claim 16, wherein the plurality of arms includes first and second sets of arms, with the first and second sets of arms intersecting at angles of less than ninety degrees.

22. A method for measuring at least one component of a small electric field generated by an object comprising:
 positioning a first, capacitive-type electrical sensor at a first position spaced from the object;
 positioning a second electrical sensor at a second position which is spaced a predetermined, fixed distance from the first position and does not depend on the object generating the small electric field;
 generating first electric potential signals from the first electrical sensor related to the electric field;
 generating second electric potential signals from the second electrical sensor related to the electric field; and
 processing the first and second electric potential signals to determine a first vector component, having both a magnitude and a direction, of the electric field.

23. The method of claim 22, wherein the first vector component is normal to the object.

24. The method of claim 22, further comprising:
 positioning at least third and fourth capacitive-type electrical sensors at respective positions spaced from the object;
 generating at least third and fourth electric potential signals from the third and fourth electrical sensors related to the electric field; and
 processing the third and fourth electric potential signals with the first and second electric potential signals to determine multiple orthogonal components of the electric field.

* * * * *